United States Patent [19]

Powers

[11] Patent Number: 5,462,556
[45] Date of Patent: Oct. 31, 1995

[54] ECTOPARASITE REMOVER AND METHOD FOR REMOVING AN ECTOPARASITE FROM A HOST ORGANISM

[76] Inventor: William J. Powers, 2044 Hillsbury Rd., Westlake Village, Calif. 91361

[21] Appl. No.: 174,151

[22] Filed: Dec. 27, 1993

Related U.S. Application Data

[63] Continuation-in-part of Ser. No. 80,777, Jun. 24, 1993, abandoned.

[51] Int. Cl.$^6$ ............................................. A61B 19/00
[52] U.S. Cl. ............................... 606/131; 119/156; 606/1
[58] Field of Search ................ 128/910, 200.14–200.23, 128/200.24, 203.12, 203.13; 119/156, 159, 160; 606/1, 131, 133

[56] References Cited

U.S. PATENT DOCUMENTS

| | | | |
|---|---|---|---|
| 1,512,486 | 10/1924 | Rhames | 128/200.14 |
| 2,691,371 | 10/1954 | Ferreira | 128/200.14 |
| 3,306,252 | 2/1967 | Knight et al. | 128/200.23 |
| 3,314,426 | 4/1967 | Carroll | 128/200.14 |
| 3,881,480 | 5/1975 | Lafourcade | 128/200.14 |
| 3,960,148 | 6/1976 | Dryden | 128/210 |
| 5,068,993 | 12/1991 | Millar | 128/200.14 |

Primary Examiner—Stephen C. Pellegrino
Assistant Examiner—Glenn Dawson
Attorney, Agent, or Firm—Timothy T. Tyson; Ted Masters

[57] ABSTRACT

An ectoparasite remover (20) and method for removing ectoparasites (56) such as ticks and leeches from a host organism (58) are disclosed. The remover (20) uses an anesthetizing gas (24) injected into a receptacle (36) to cause the ectoparasite (56) to voluntarily withdraw from the host organism (58).

35 Claims, 6 Drawing Sheets

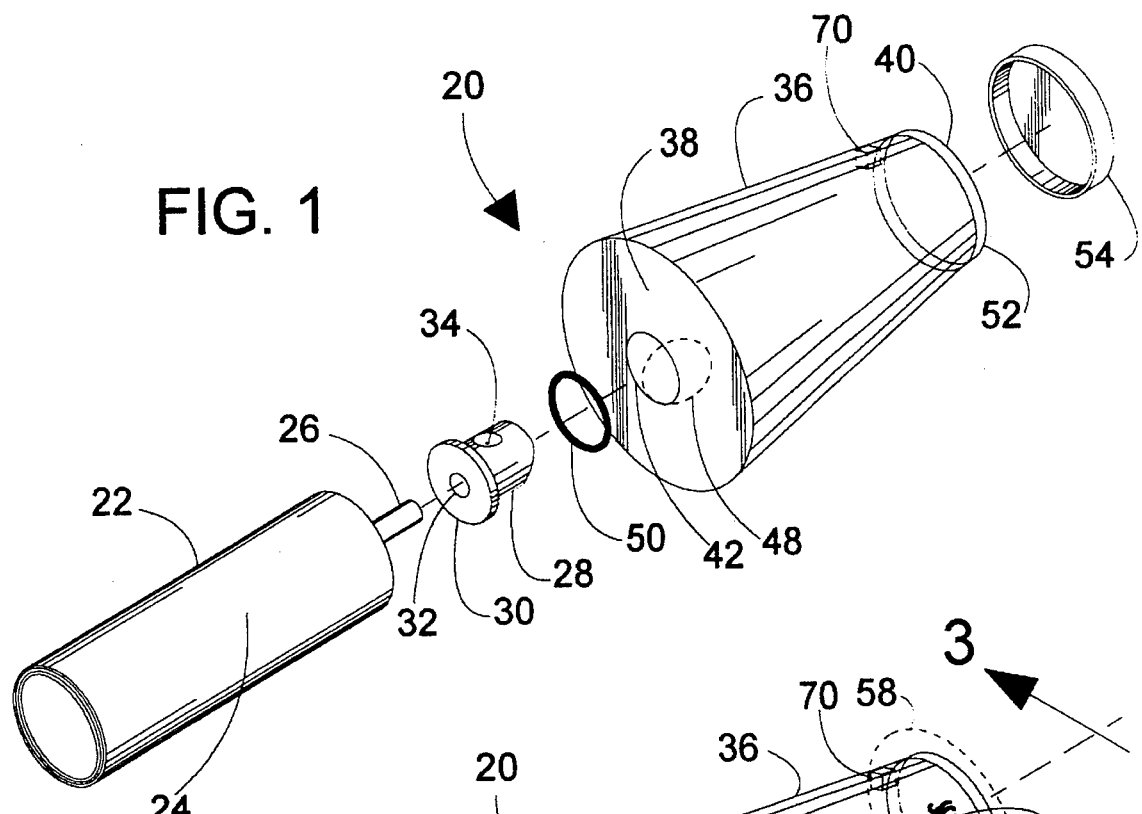
FIG. 1
FIG. 2
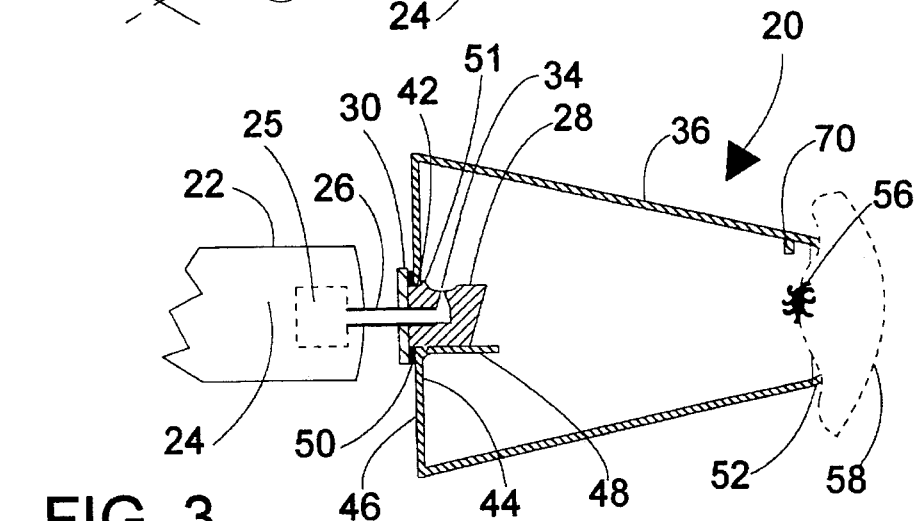
FIG. 3

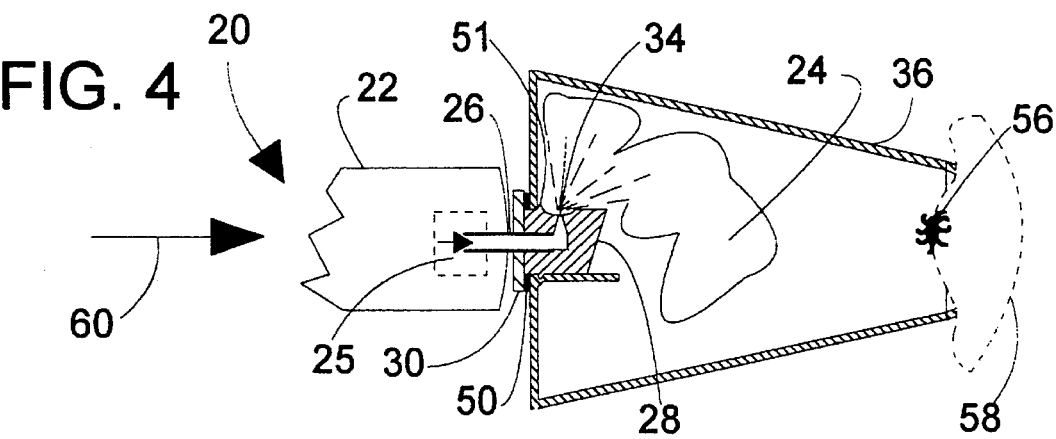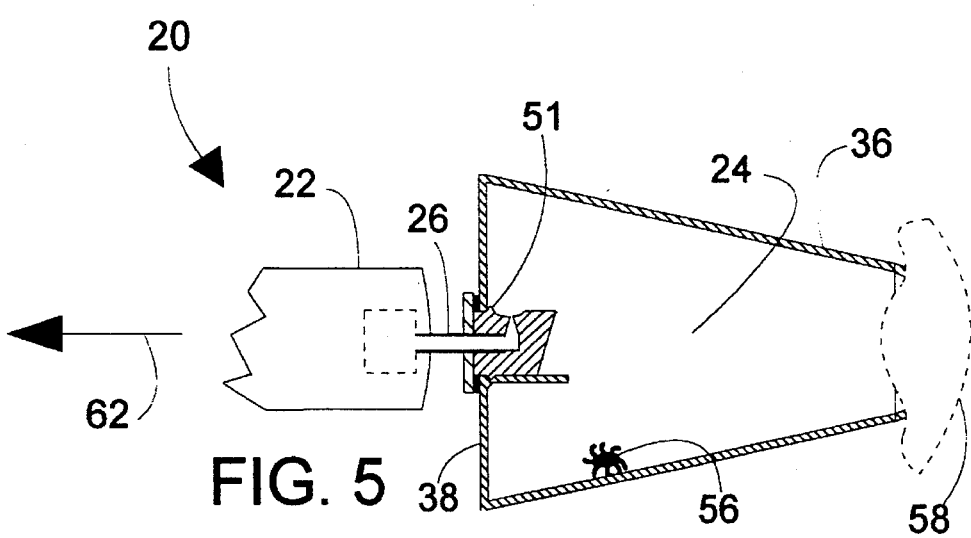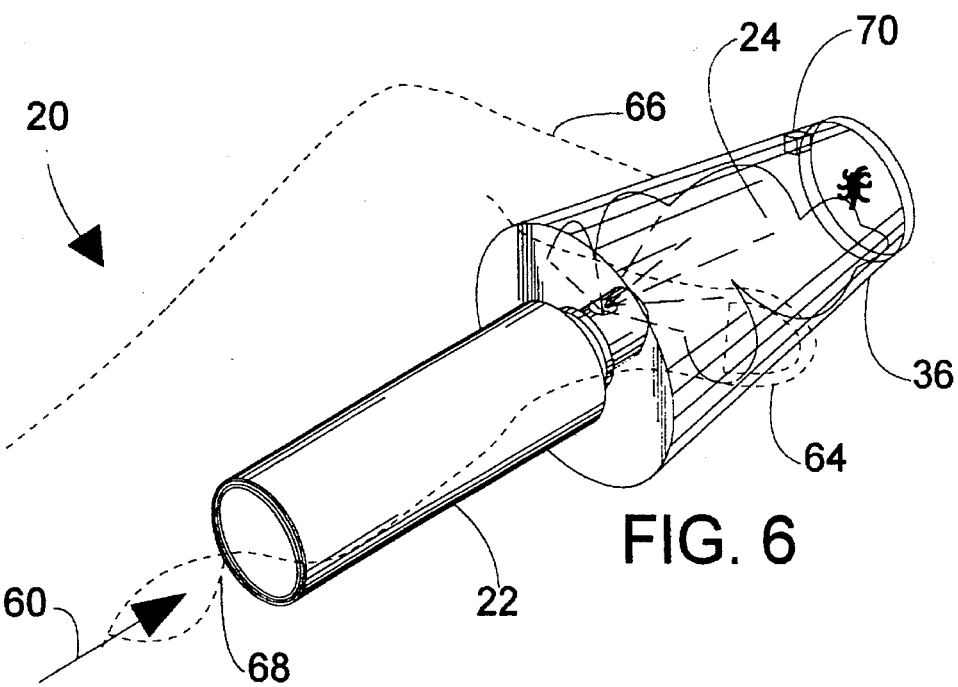

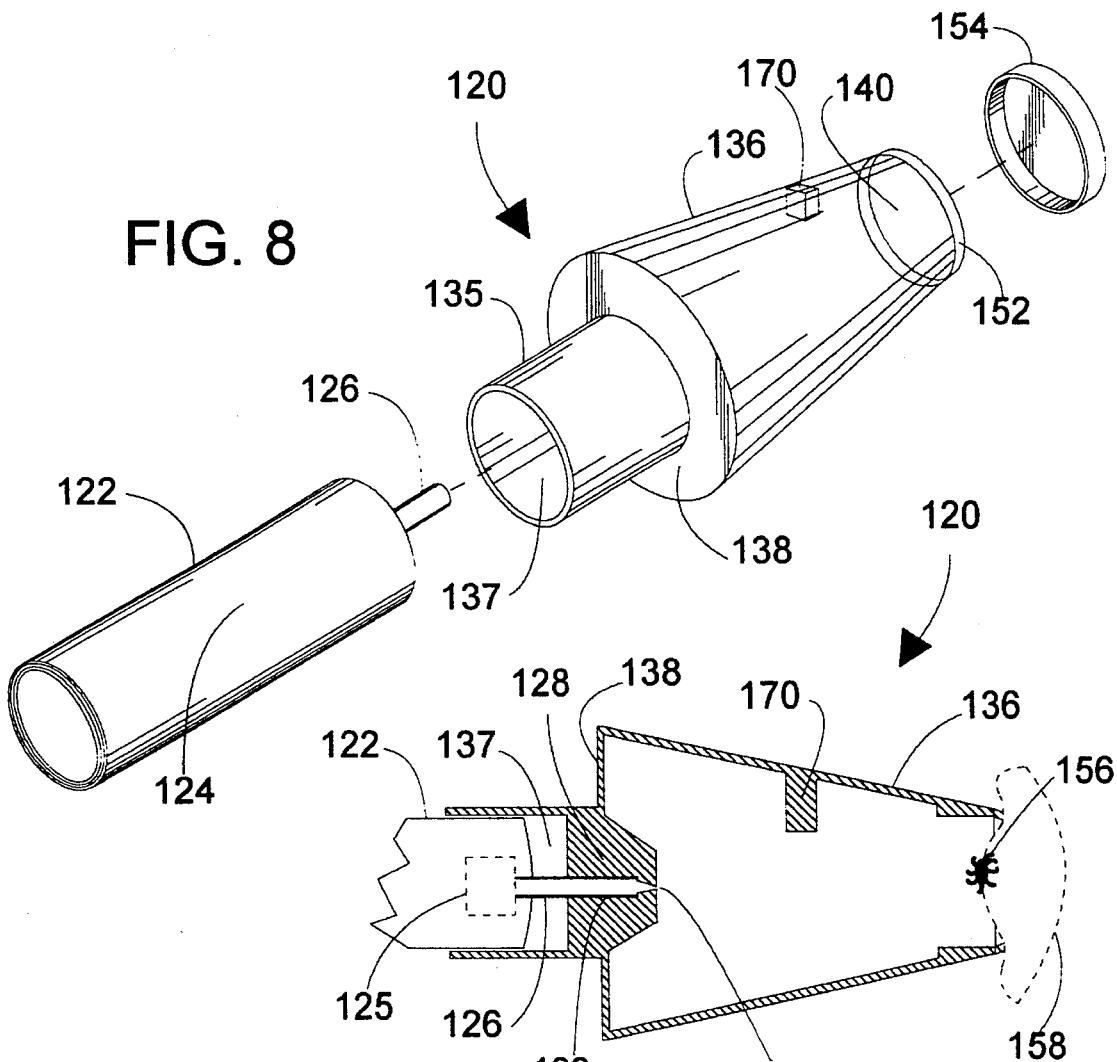
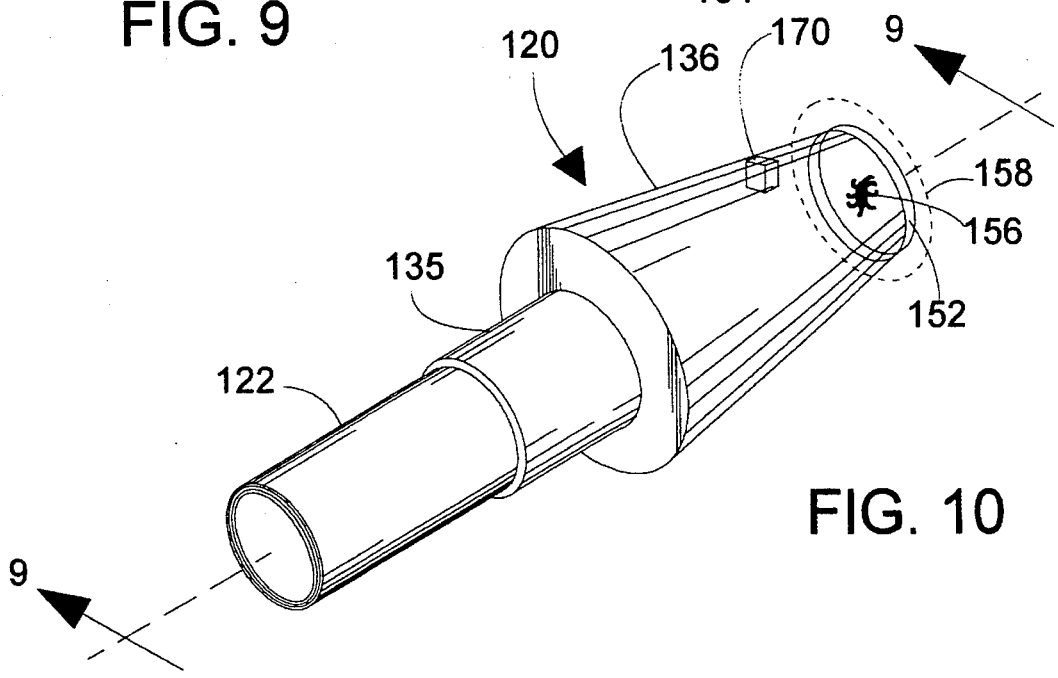

ECTOPARASITE REMOVER AND METHOD FOR REMOVING AN ECTOPARASITE FROM A HOST ORGANISM

CROSS REFERENCE TO RELATED APPLICATION

This is a continuation-in-part of application Ser. No. 08/080,777 filed Jun. 24, 1993 now abandoned.

TECHNICAL FIELD

The present invention relates to the field of preventive medicine. The present invention pertains to a remover and method for removing an ectoparasite from a host organism, and more particularly to a remover and method which employs anesthetizing gas combined with a specially designed receptacle to effect the removal.

BACKGROUND ART

It has long been established that ticks are vectors of many diseases throughout the world. Examples include: Tick-borne Hemorrhagic Fever in Russia; Tick Paralysis in Australia; Tick-borne Rickettsia in South Africa; Rocky Mountain Spotted Fever and Colorado Tick Fever in the Rocky Mountain States; Tularemia in Montana; Tick-Borne Encephalitis in the Mid-Western States; and most importantly Lyme Disease predominately in the Eastern United States.

It is now a well known medical fact that most people infected with Lyme Disease do not contract the disease because they were simply bitten by a tick, but rather because of improper tick removal. The reason is that the microorganism that causes Lyme disease resides within the gut of the tick. Improper removal of the tick causes the tick to regurgitate internal fluids from the gut and thereby inject the microorganism into the host through the tick's hypostome (proboscis or mouth parts).

Therefore, the most commonly used removal methods such as fingers, tweezers, mechanical instruments that can rotate the tick, heat, petroleum jelly, chemicals, and depilating devices can actually occasion the spread of tick-borne diseases by causing the tick to regurgitate the disease-bearing microorganism into the host.

Using fingers to dislodge the tick can cause the tick to regurgitate, and can additionally result in leaving all or portions of the tick's hypostome (proboscis or mouth parts) in the host. This removal method can also result in the spread of disease through subsequent contact with the remover's contaminated fingers and hands.

Tweezers, which are common devices for tick removal, can easily squeeze the tick's abdomen and thereby inject the microorganism into the host. This method can additionally leave the tick's hypostome (proboscis or mouth parts) in the host which may lead to secondary inflammation and infection.

The use of any implement to remove a tick by rotating the tick's body is perhaps based upon the erroneous conception that the tick's hypostome (proboscis or mouth parts) is corkscrew-shaped and can therefore be removed by unscrewing. Actually, the mouth parts of the hypostome (proboscis) include retractable barbs called chelicerae which are similar to miniature circular saw blade which reside upon the hypostome. Additionally, a hardening substance exuded by the tick tightly holds the proboscis and associated mouth parts to the host. Any rotation, pulling, pushing or twisting of the tick's body is likely to leave these mouth parts in the skin or flesh of the host. This may lead to complications due to secondary infection.

Using heat or electric shock can cause the tick to regurgitate prematurely and can also burn the skin or flesh of the host organism.

Petroleum jelly slowly suffocates the tick and allows time for the tick to regurgitate. The slowness of this method is due to the difficulty of coating the tick's entire body underneath and above with the jelly. Completely coating the tick with petroleum jelly is even more difficult in areas containing hair.

Chemical agents such as kerosene, gasoline, chloroform, and carbon tetrachloride are hazardous and toxic to the human or animal host. Further, most of these chemicals are highly flammable, can cause skin irritation, and entice the tick to regurgitate.

Methods including the use of hypodermic needles or scalpels for tick removal can prick or abrade the skin causing secondary infection and possible scaring.

For the reasons stated, all of the methods identified in the above paragraphs are unsuitable for removing ticks quickly, safely, comfortably, and most importantly completely. It is important to note that the Centers for Disease Control (CDC) in Documents #361701 and #361703 dated 19 Nov. 1992 specifically admonish the use of burning, hot objects such as matches or cigarettes, coating with anything such as nail polish remover or vaseline, or other methods to remove ticks.

Other ectoparasites such as leeches differ somewhat in the specific manner of attachment to the host and methods of disease transmission. Nonetheless, improper removal procedures can result in the same undesirable consequences encountered with ticks.

U.S. Pat. No. 4,213,460 employs a combination of forceps, a thermal element, and chemical agents to remove a parasite. U.S. Pat. No. 5,116,347 utilizes a mechanical removal means.

DISCLOSURE OF INVENTION

The present invention is directed to a novel remover and method for removing an ectoparasite from a host organism. The present invention employs an anesthetizing gas to safely, comfortably, and most importantly completely, remove embedded ectoparasites such as ticks or leeches from the skin or flesh of human or animal host organisms especially in sensitive and difficult to reach areas containing hair.

In accordance with a preferred embodiment of the invention, a receptacle having a gas spraying orifice is connected to a gas producing means for supplying an anesthetizing gas such as carbon dioxide or nitrogen.

In accordance with another preferred embodiment of the invention, a sealing means placed around the ectoparasite tightly connects the open end of the receptacle to the host organism. When the gas producing means is activated, gas enters the receptacle and quickly anesthetizes the ectoparasite.

In accordance with another preferred embodiment of the invention, the low temperature created by the rapid expansion of the gas enhances the removal process.

In accordance with another preferred embodiment of the invention, the receptacle is transparent allowing the user to view the removal process and easily determine when the ectoparasite releases from the host.

In accordance with another important aspect of the invention, the receptacle is tapered. The taper of the receptacle permits the invention to be used in a more upright position while gravity causes the ectoparasite to fall away from the host and into the receptacle.

In accordance with another preferred embodiment of the invention, a closure means such as a cap or pressure sensitive tape is provided that can be placed over the open end of the receptacle to contain the ectoparasite upon removal.

In accordance with a feature of the invention, the invention uses a non-toxic anesthetizing gas rather than any of the methods which are specifically not recommended by the Centers for Disease Control.

In accordance with a feature of the invention, the anesthetizing gas causes the ectoparasite to both rapidly and voluntarily release from the host, not allowing time for the ectoparasite to regurgitate microorganisms, and not leaving mouth parts in the host. This feature minimizes potential disease transmission to the host.

In accordance with a feature of the invention, the anesthetizing gas is non-toxic and non-flammable and therefore cannot irritate or damage the skin of the host, and can also be utilized in areas having high fire danger.

In accordance with a feature of the invention, the removal process does not harm the host, the environment, or the ectoparasite.

Other features and advantages of the present invention will become apparent from the following detailed description, taken in conjunction with the accompanying drawings, which illustrate, by way of example, the principles of the invention.

BRIEF DESCRIPTION OF DRAWINGS

FIG. 1 is an exploded perspective view of the remover in accordance with the present invention;

FIG. 2 is a perspective view of the remover in the ready for use configuration;

FIG. 3 is a cross-sectional view of the remover along the line 3—3 of FIG. 2 prior to the release of anesthetizing gas;

FIG. 4 is a cross-sectional view of the remover along the line 3—3 of FIG. 2 during the release of the anesthetizing gas;

FIG. 5 is a cross-sectional view of the remover along the line 3—3 of FIG. 2 after the ectoparasite has been anesthetized;

FIG. 6 is a perspective view of the remover during the release of the anesthetizing gas;

FIG. 8 is an exploded perspective view of a third embodiment;

FIG. 9 is a cross-sectional view of the third embodiment along the line 9—9 of FIG. 10 prior to the release of anesthetizing gas;

FIG. 10 is a perspective view of the third embodiment in the ready for use configuration;

BEST MODES FOR CARRYING OUT THE INVENTION

Figure 6A:
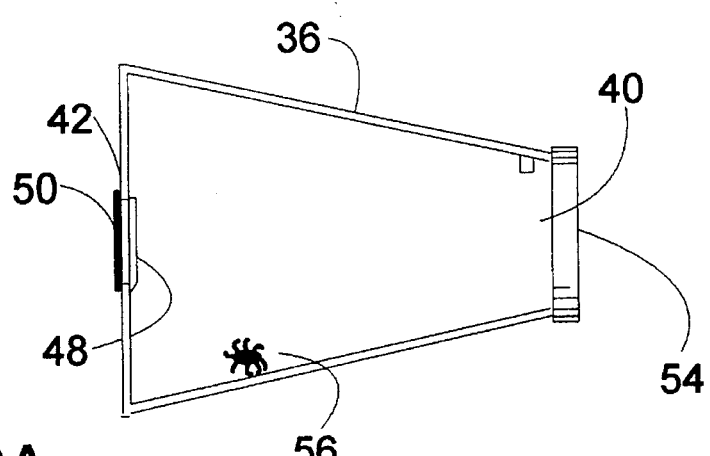
FIG. 6A is a cross-sectional view of the receptacle with the anesthetized ectoparasite inside.

Referring initially to FIG. 1 there is illustrated an exploded perspective view of a remover for removing an ectoparasite from a host organism in accordance with the present invention, generally designated as 20. The remover 20 consists of a light weight gas producing means in the form of a pressurized gas container or cylinder 22 containing a pressurized anesthetizing gas 24 for anesthetizing an ectoparasite and a receptacle 36 for containing the ectoparasite and gas. The cylinder 22 has a pressure activated release valve 25 (FIG.3), and a hollow valve stem 26 longitudinally connected to the release valve. The release valve 25 is spring loaded so that it is normally closed with the valve stem 26 protruding outwardly to its outward limit. The anesthetizing gas 24 in the cylinder is highly pressurized so that it exists in a liquid state. Other gas producing means may utilize gas stored in a gaseous state. Carbon dioxide or nitrogen have been found to be useful anesthetizing gases. A plunger 28 having a flange 30 is connected to the valve stem 26 by the valve stem receiving hole 32 which mounts over and snugly receives the valve stem 26. The plunger 28 has a gas spraying orifice 34 internally connected to the valve stem receiving hole 32. When the plunger 28 is pushed toward the cylinder 22, the valve stem 26 activates the pressure activated valve 25 which releases the anesthetizing gas 24 through the valve stem 26 and valve stem receiving hole 32 to the gas spraying orifice 34 which emits the anesthetizing gas 24.

The tapered receptacle 36 is fabricated of clear plastic and has a closed wide end 38, an open narrow end 40, a hole 42 in the closed wide end 38 sized to snugly receive the plunger 28, an outside surface 46 (FIG. 3), and an inside surface 44 (FIG. 3). A flap 48 is coupled to the inside surface 44 where it resiliently and retractably covers hole 42. A first gasket 50 is positioned adjacent the outside surface 46 of the closed wide end 38 surrounding hole 42. In the embodiment shown, the first gasket 50 is a rubber "0" ring. The first gasket 50 is sized so that the flange 30 cannot pass through and will be engaged by the first gasket 50. A second gasket 52 is coupled to the open narrow end 40. A cap 54 is removably connected to the open narrow end 40 and is sized to snugly fit over the open narrow end 40. After the ectoparasite 56 has been anesthetized, the cap may be placed over the open narrow end 40 and the plunger 28 removed allowing the flap 48 to close the hole 42 thereby containing the ectoparasite 56 within the receptacle 36 until proper disposal can be made. One disposal mode is to totally discard the entire receptacle 36 and cap 54 with the contained ectoparasite 56. This method minimizes possible contamination of the user.

FIG. 2 is a perspective view of the remover 20 in the ready for use configuration. The cylinder 22 containing the anesthetizing gas 24 has been connected to the plunger 28. The plunger 28 is inserted into hole 42 (FIG. 1) in the receptacle 36 causing the flap 48 (FIG. 1) to resiliently and retractably move out of the way. The second gasket 52 is placed around the ectoparasite 56 and is pressed firmly against the host organism 58 to form a tight seal so that the anesthetizing gas 24 cannot escape from the receptacle 36. It is noted that the receptacle 36 is transparent. This feature allows the user to view the ectoparasite 56 throughout the removal process and easily determine where to position the open end 40 around the ectoparasite 56 and to see when the anesthetizing process is complete and the ectoparasite 56 has released from the host.

FIG. 3 is a cross-sectional view of the remover along the line 3—3 of FIG. 2 in the ready for use configuration prior to the release of anesthetizing gas. The plunger 28 is connected to the valve stem 26, which is in turn connected to the pressure activated release valve 25. The plunger 28 has been longitudinally inserted into the hole 42 until the flange 30 firmly presses against the first gasket 50 forming a tight seal. A small ridge 51 formed around the plunger 28 (see also FIG. 7) provides a snap mechanism for holding the plunger 28 within the hole 42 which keeps the receptacle 20 and cylinder 22 together facilitating use of the remover by one hand. The flap 48 resiliently pivots away from the hole 42 as the plunger 28 is inserted. The second gasket 52 is positioned around the ectoparasite 56 and firmly pressed against the skin of the host organism 58 to form a tight seal.

FIG. 4 is a cross-sectional view of the remover 20 along the line 3—3 of FIG. 2 during the release of anesthetizing gas 24. The cylinder 22 is manually moved in direction 60 while the receptacle 36 remains stationary. The movement causes the plunger 28 to depress the valve stem 26 which applies pressure to the pressure activated release valve 25, thus releasing the anesthetizing gas 24 through the valve stem 26 and the gas spraying orifice 34. The anesthetizing gas 24 fills the receptacle 36 and quickly anesthetizes the ectoparasite 56. In addition, the anesthetizing gas 24 expands upon release from its liquid or gaseous state in the cylinder 22 causing it to cool and rapidly lower temperature within the receptacle 36 including the temperature of the ectoparasite. This cooling effect enhances and quickens the removal process. The anesthetizing gas 24 by itself and in combination with the reduced temperature and reduced availability of oxygen within receptacle 36 causes the ectoparasite 56 to both rapidly and voluntarily release and retract its mouth parts from the host organism 58 and fall into the receptacle not allowing time for the ectoparasite to regurgitate disease-bearing microorganisms and not leaving mouth parts in the host which might cause infection. The anesthetizing gas 24 is non-toxic and therefore does not irritate the skin of the host 58. The anesthetizing gas 24 complies with the admonitions of the Centers for Disease Control against using coatings or heat as tick removal methods. The anesthetizing gas 24 is non-flammable and does not support combustion and therefore does not present a danger if used in areas of high fire danger. Additionally, the removal process does not harm the host organism 58, the environment, or the ectoparasite 56.

FIG. 5 is a cross-sectional view of the remover 20 along the line 3—3 of FIG. 2 after the ectoparasite has been anesthetized. Manual force has been used to release the gas 24, and the cylinder 22 has returned to its ready for use configuration in the direction 62 due to the spring loading of the valve stem 26. The anesthetizing gas 24 has filled the receptacle 36 and has caused the ectoparasite 56 to voluntarily detach from the host 58. Gravity has caused the ectoparasite 56 to fall down into the receptacle and the taper of the receptacle has caused it to slide away from the host toward the closed wide end 38. The taper permits the remover 20 to be used in a more upright position than would otherwise be possible.

FIG. 6 is a perspective view of the remover 20 during the release of the anesthetizing gas 24. The receptacle 36 is grasped between the thumb 64 and the index finger 66. The cylinder 22 is pressed against the heal of the hand 68 so that the heal of the hand 68 can exert longitudinal force upon the cylinder 22 in direction 60 and thereby initiate the release of the anesthetizing gas 24. The taper of the receptacle 36 permits the thumb 64 and index finger 66 to more securely hold the receptacle 36 against the force being applied by the heal of the hand 68. It is also possible for the user to utilize two hands during the removal process.

FIG. 6A is a cross-sectional view of the receptacle 36 with the anesthetized ectoparasite 56 inside ready for disposal. The plunger has been removed allowing the flap 48 to close and cover the hole to prevent the ectoparasite from escaping when it revives. The cap 54 has been placed over the open end 40 to prevent the ectoparasite from escaping from this end. The entire assembly shown in FIG. 6A can be disposed of as a unit if desired in order to eliminate any possible contact with the ectoparasite or it can be used to transport the ectoparasite to another location where the ectoparasite can be removed and the plastic receptacle recycled.

Figure 6B:
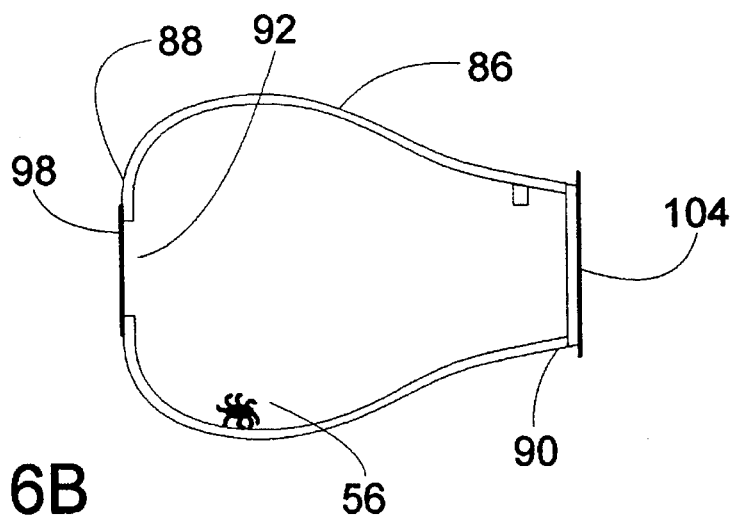
FIG. 6B is a cross-sectional view of a second embodiment of the remover similar to FIG. 6A.

FIG. 6B is a cross-sectional view of a second embodiment of a receptacle 86 with the anesthetized ectoparasite 56 inside ready for disposal similar to FIG. 6A. The receptacle 86 is inexpensively fabricated of blow molded plastic in a pear shape having a closed wide end 88 with a hole 92 for a plunger such as the plunger 28 of the first embodiment and a narrow open end 90. Instead of the flap and cap closure means of the first embodiment, the closure means of the second embodiment includes a first pressure sensitive tape 98 used to cover the hole 92 in the closed wide end 88 and a second pressure sensitive tape 104 used to cover the open narrow end 90. All other elements of the second embodiment are the same as in the first embodiment and it is used in the same way. After the ectoparasite has been anesthetized and has fallen off the host organism, the plunger is removed from the hole 92 and the first pressure sensitive tape 98 is placed over the hole 92 to close and cover the hole to prevent the ectoparasite from escaping when it revives. The second pressure sensitive tape 104 has been placed over the open narrow end 90 to prevent the ectoparasite from escaping from this end. The entire assembly shown in FIG. 6B can be disposed of as a unit if desired in order to eliminate any possible contact with the ectoparasite or it can be used to transport the ectoparasite to another location where the ectoparasite can be removed and the plastic receptacle recycled.

Figure 7:
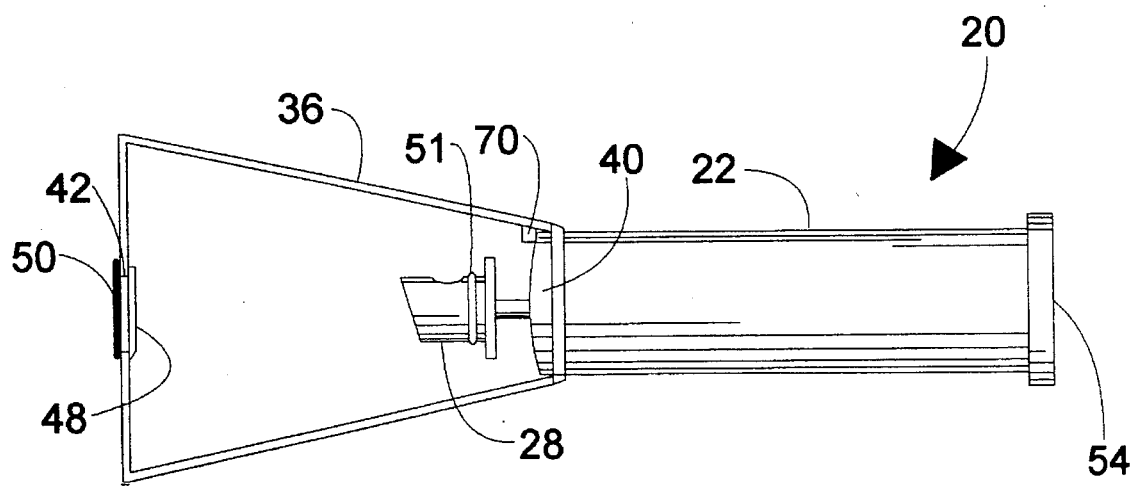
FIG. 7 is a side view showing the first embodiment of the remover in the storage or transport configuration.

FIG. 7 is a side view showing the remover 20 in the storage or transport configuration. The cylinder 22 and attached plunger 28 have been removed from hole 42 in the receptacle 36. The flap 48 has returned to the closed position thus covering hole 42. The plunger 28 and cylinder 22 are inserted into the narrow open end 40 of the receptacle 36. The narrow open end 40 is sized to snugly receive cylinder 22. A stop 70 limits the depth to which the cylinder 22 may be inserted into the receptacle 36 to prevent the plunger 28 from hitting the other end and inadvertently discharging gas. Cap 54 snugly fits over the end of cylinder 22.

FIG. 8 is an exploded perspective view of a third embodiment of the remover, generally designated as 120. FIG. 9 is a cross-sectional view of the third embodiment. The remover 120 consists of a gas producing means for supplying anesthetizing gas 124. The gas producing means includes a pressurized gas container 122 containing an internal pressure activated release valve 125 and a hollow valve stem 126 internally connected to the release valve 125. The valve stem 126 is longitudinally connected to the gas container 122 and externally protrudes therefrom. The valve stem 126 is spring loaded so that it is urged to its extreme outwardly protruding position. Alternate gas sources could serve equally well and could include externally connected gas sources containing anesthetics in either the liquid or gaseous state such as storage containers, tanks, or compressors and their associated hoses and related attachment devices. Carbon dioxide or nitrogen have been found to be useful anesthetizing gases 124, however any other gas that can anesthetize an ectoparasite could also be used. A receptacle 136 has a gas spraying orifice 134 at a closed end 138. The closed end 138 further includes a plunger 128 having a first cavity 133 internally connected to the gas spraying orifice 134 and a second cavity 137 connected to the first cavity 133 formed by the integral attachment of a sleeve 135 to the closed end 138. The gas container 122 is inserted into the sleeve 135 until the hollow valve stem 126 is snugly received by the first cavity 133 and the gas container 122 is snugly received by the second cavity 137. When the gas container 122 is fully inserted into the sleeve 135, the external end of the valve stem 126 is in contact with the gas spraying orifice 134. Opposite the closed end 138 is an open end 140. A sealing means 152 for sealing the receptacle 136 to the host organism 158 is coupled to the open end 140. In the embodiment shown, the sealing means 152 is a gasket which can be formed from any suitable material such as rubber, plastic, or synthetic foam. The sealing means 152 can also consist of a hard material, and may simply be an extension of the material which forms the receptacle 136. In the embodiment shown, the sealing means 152 is planar, however other shapes are also possible. In a preferred embodiment, the receptacle 136 is formed from transparent material such as clear plastic thus allowing the user to view the ectoparasite while placing the open end 140 around it and during the removal process when it is easy to see when the ectoparasite 156 has been anesthetized and releases from the host. In a preferred embodiment, the receptacle 136 is tapered wherein the closed end 138 has a first cross-sectional area that is larger than the second cross-sectional area of the open end 140. In the shown embodiment, both the first cross-sectional area and the second cross-sectional area are circular. A cap 154 is sized to removably fit over the open end 140. The cap 154 is used to contain the ectoparasite 156 within the receptacle 136 after it has fallen from the host organism.

FIG. 10 is a perspective view of the remover 120 in the ready for use configuration. The sealing means 152 has been positioned around the ectoparasite 156 and firmly pressed against the host organism 158.

Figure 11:
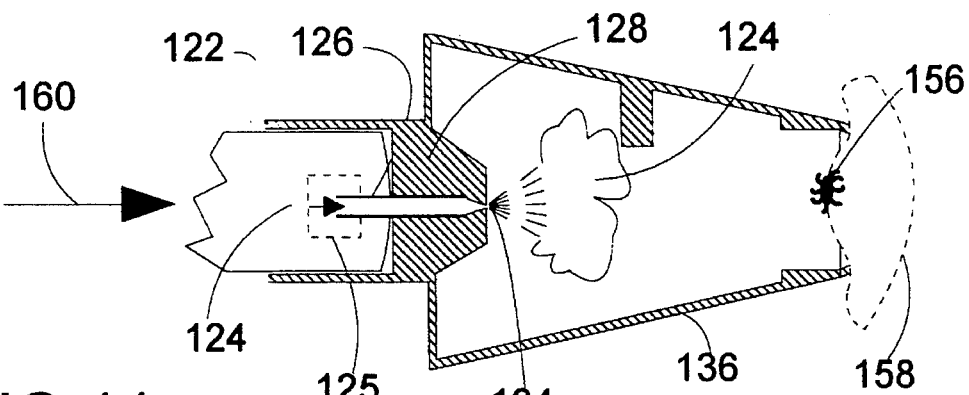
FIG. 11 is a cross-sectional view of the third embodiment along the line 9—9 of FIG. 10 during the release of anesthetizing gas.

FIG. 11 is a cross-sectional view of the remover 120 during the release of anesthetizing gas 124. The gas container 122 is manually moved in direction 160 while the receptacle 136 and integral plunger 128 remain stationary. The movement of the pressurized gas container 122 causes the hollow valve stem 126 to move further into the gas container 122 and activate the pressure activated release valve 125, thus releasing the pressurized anesthetizing gas 124 through the valve stem 126, through the gas spraying orifice 134, and into the receptacle 136.

Figure 12:
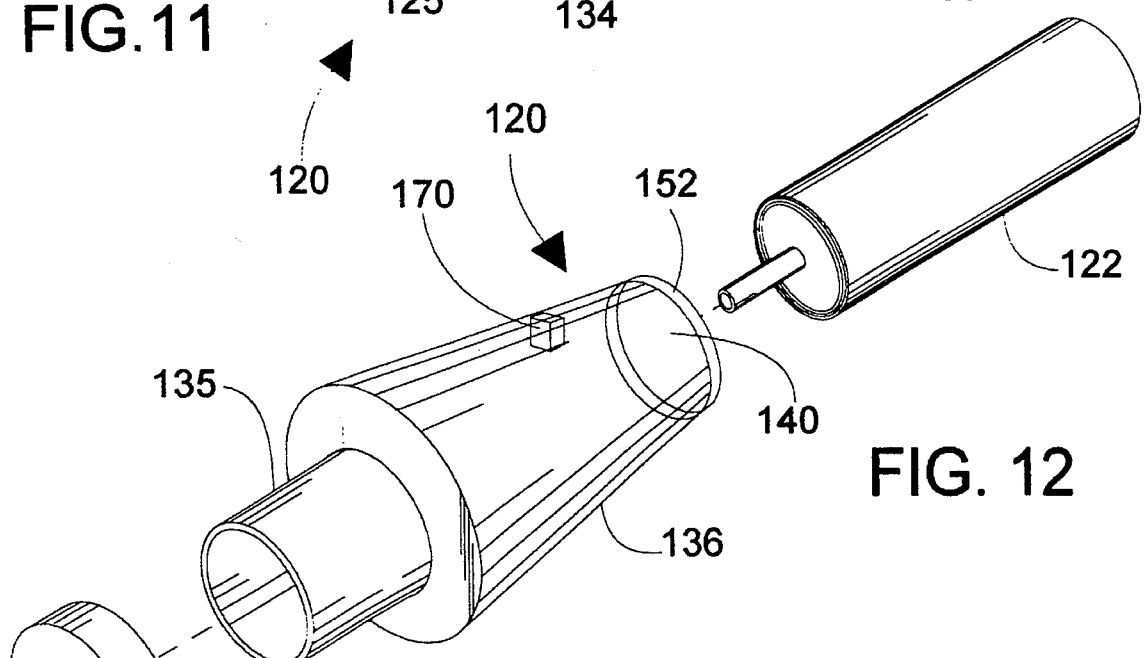
FIG. 12 is an exploded perspective view of the third embodiment in the storage or transport configuration.

FIG. 12 is an exploded perspective view of the remover 120 in the storage or transport configuration. Gas container 122 is reversed and moved to align with the open end 140 of the receptacle 136. Cap 154 is moved to align with the sleeve 135. The open end 140 is sized to snugly receive the gas container 122. The outside of the sleeve 135 is sized to snugly receive the inside of the cap 154.

Figure 13:
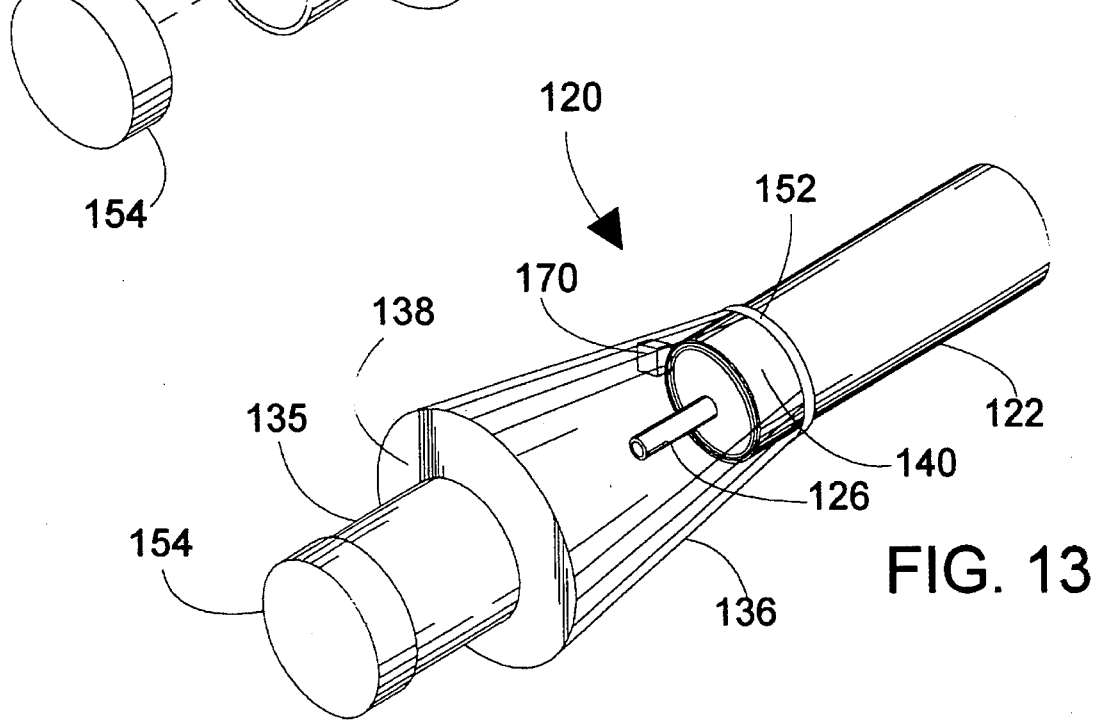
FIG. 13 is a perspective view of the third embodiment in the storage or transport configuration.

FIG. 13 is a perspective view of the remover 120 in the storage or transport configuration. The gas container 122 has been inserted into the open end 140. Stop 170 limits the insertion distance so that the valve stem 126 cannot be engaged by the closed end 138 of the receptacle 136. The cap 154 has been installed over the sleeve 135.

Figure 14:
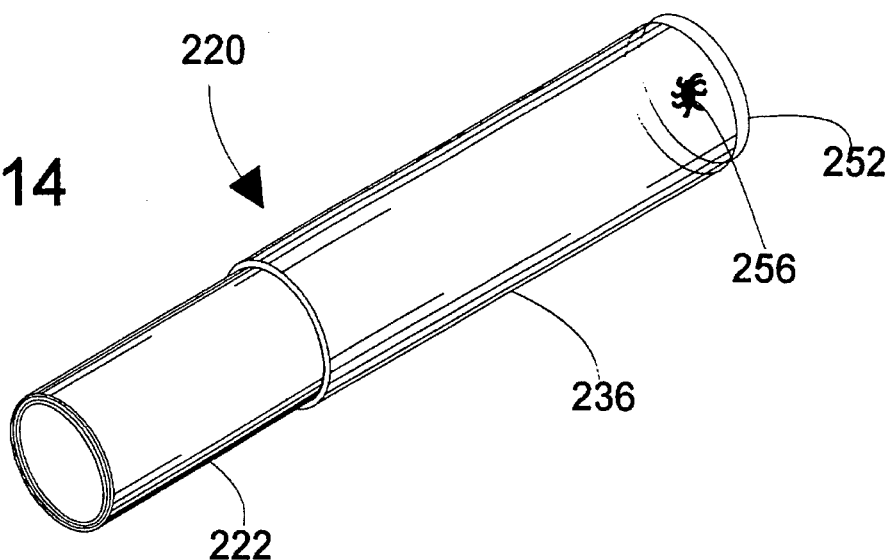
FIG. 14 is a perspective view of a fourth embodiment.

FIG. 14 is a perspective view of a fourth embodiment of the remover, generally designated as 220. Pressurized gas container 222 is inserted into straight walled receptacle 236. Sealing means 252 is positioned over ectoparasite 256. The receptacle can be tapered as in FIG. 8, straight as in FIG. 14, or formed in any other convenient shape such as right angled or curved.

Figure 15:
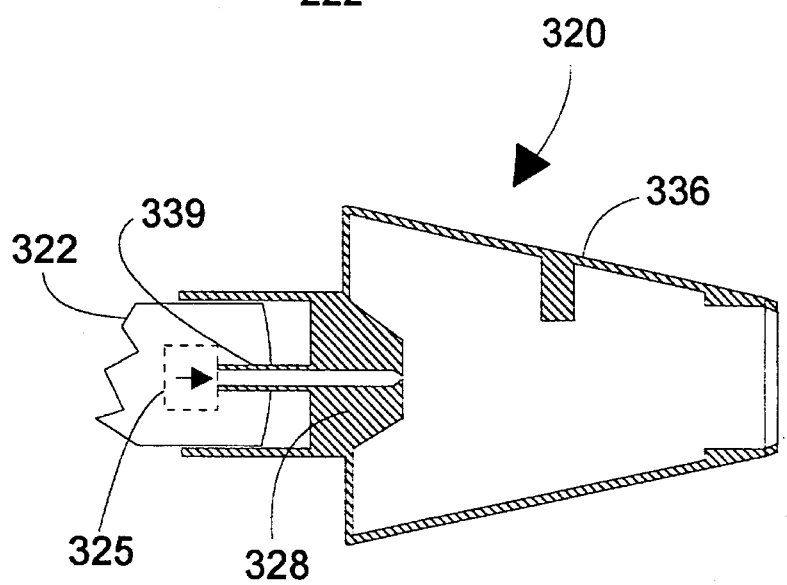
FIG. 15 is a cross-sectional view of a fifth embodiment.

FIG. 15 is a cross-sectional view of a fifth embodiment of the remover, generally designated as 320. In this embodiment the plunger 328 includes a protruding hollow nozzle 339. The nozzle 339 activates the pressure activated release valve 325 when the gas container 322 is moved toward the receptacle 336.

Figure 16:
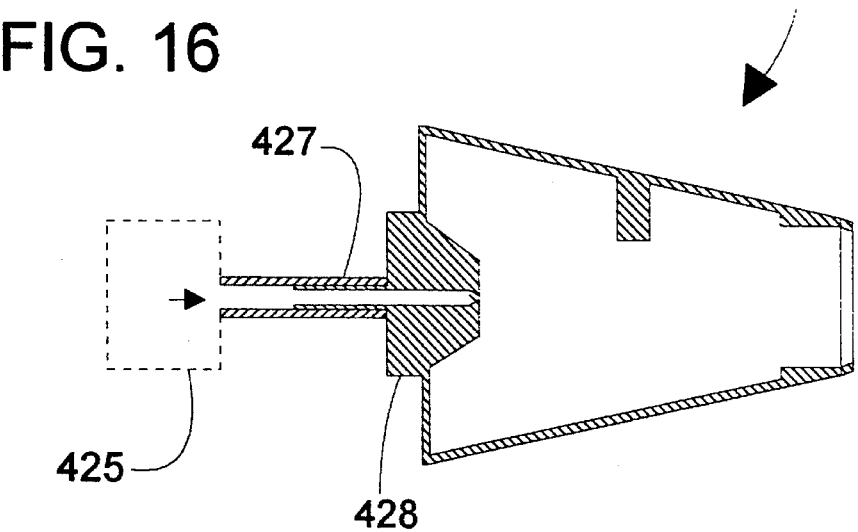
FIG. 16 is a cross-sectional view of a sixth embodiment.

FIG. 16 is a cross-sectional view of a sixth embodiment of the remover, generally designated as 420. Instead of having a pressurized gas container, an alternate gas producing means such as an external tank 425 is connected by a hose or tube 427 to the plunger 428.

The preferred embodiments of the invention described herein are exemplary and numerous modifications, dimensional variations, and rearrangements can be readily envisioned to achieve an equivalent result, all of which are intended to be embraced within the scope of the appended claims.

I claim:

1. A remover for removing an ectoparasite from a host organism, comprising:

a receptacle having an open end;

plunger coupled to said receptacle and having a gas spraying orifices; and, an anesthetizing gas producing means having anesthetizing gas and a pressure activated release valve coupled to said plunger for injecting said anesthetizing gas through said gas spraying orifice into said receptacle when pressure is applied by said plunger on said pressure activated release valve.

2. The remover according to claim 1, further comprising a sealing means coupled to said open end for sealing said open end to the host organism.

3. The remover according to claim 2, wherein said sealing means is a gasket.

4. The remover according to claim 1, wherein said gas producing means includes a pressurized gas container.

5. The remover according to claim 4, wherein said pressurized gas container includes a pressure activated release valve.

6. The remover according to claim 1, wherein said receptacle is formed from transparent material.

7. The remover according to claim 6, wherein said transparent material is plastic.

8. The remover according to claim 1, wherein said receptacle further includes a closed end, said closed end has a first cross-sectional area, said open end has a second cross-sectional area, and said first and second cross-sectional areas are circular.

9. The remover according to claim 8, wherein said first cross-sectional area is larger than said second cross-sectional area.

10. The remover according to claim 1, further including a cap sized to removably fit over said open end.

11. The remover according to claim 1, wherein said anesthetizing gas is carbon dioxide.

12. The remover according to claim 1, wherein said anesthetizing gas is nitrogen.

13. The remover according to claim 1 wherein said plunger is positioned on said gas producing means and said receptacle further includes a closed end having a hole closed by said plunger inserted through said hole into said receptacle.

14. The remover according to claim 13 further including a snap mechanism for holding said plunger in said hole.

15. The remover according to claim 13 wherein said receptacle further includes a closure means for closing said hole after said plunger has been removed and for closing said open end to prevent escape of the ectoparasite from said receptacle.

16. The remover according to claim 15 wherein said receptacle further includes an inside surface and said closure means includes a flap coupled to said inside surface of said closed end retractably covering said hole.

17. The remover according to claim 16 wherein said closure means further includes a cap for covering said open end.

18. The remover according to claim 15 wherein said closure means includes a first pressure sensitive tape for covering said hole and a second pressure sensitive tape for covering said open end.

19. The remover according to claim 1 wherein said receptacle further includes a closed end and said plunger is integrally formed with said closed end.

20. The remover according to claim 1, wherein said receptacle further includes a closed end and said closed end has a sleeve sized to snugly receive said pressurized gas container.

21. A remover for removing an ectoparasite from the skin of a host organism, comprising:
    a pressurized gas container containing a gas for anesthetizing the ectoparasite and having a hollow valve stem connected to a valve for releasing said gas;
    a plunger attached to said valve stem, said plunger having a flange;
    a clear plastic tapered receptacle having:
        a closed wide end having a hole receiving said plunger;
        an open narrow end opposite said closed wide end;
        an outside surface;
        an inside surface; and,
        a flap coupled to said inside surface of said closed wide end of said receptacle, said flap retractably covering said hole;
    a first gasket surrounding said hole on said outside surface of said receptacle and sized to engage said flange;
    a second gasket coupled to said narrow open end of said receptacle; and,
    a cap removably connected to said receptacle and sized to fit over said narrow open end of said receptacle;
    whereby, when said pressurized gas container is pushed toward said receptacle, said flange engages said first gasket causing said plunger to depress said valve releasing said gas from said pressurized gas container into said receptacle.

22. A method for removing an ectoparasite from a host organism, comprising the steps of:

providing a receptacle having an open end and a gas producing means for injecting anesthetizing gas into said receptacle;

positioning said open end around the ectoparasite;

pressing said open end against the host organism;

activating said gas producing means thereby injecting anesthetizing gas into said receptacle;

waiting until the ectoparasite is anesthetized and falls into said receptacle; and, removing said receptacle with the anesthetized ectoparasite from the host organism.

23. The method for removing an ectoparasite from a host organism according to claim 22, wherein said providing step further includes a closure means for closing said receptacle after the anesthetized ectoparasite is inside, and further including the step of activating said closure means.

24. The method for removing an ectoparasite from a host organism according to claim 23 wherein said providing step further includes said receptacle having a closed end, said closed end having a hole, and said closure means including a flap retractably closing said hole and a cap for covering said open end, and further including the steps of allowing said flap to close said hole and placing said cap over said open end.

25. The method for removing an ectoparasite from a host organism according to claim 23, wherein said providing step further includes said receptacle having a closed end, said closed end having a hole, and said closure means including a first pressure sensitive tape for covering said hole and a second pressure sensitive tape for covering said open end, and further including the steps of placing said first pressure sensitive tape over said hole, placing said second pressure sensitive tape over said open end.

26. A remover for removing an ectoparasite from a host organism, comprising:
    a receptacle having an open end;
    a plunger coupled to said receptacle and having a gas spraying orifice;
    an anesthetizing gas producing means coupled to said plunger having anesthetizing gas for injection through said gas spraying orifice into said receptacle; and,
    a gasket coupled to said open end for sealing said open end to the host organism.

27. A remover for removing an ectoparasite from a host organism, comprising:
    a receptacle having an open end;
    a plunger coupled to said receptacle and having a gas spraying orifice;
    an anesthetizing gas producing means coupled to said plunger having anesthetizing gas for injection through said gas spraying orifice into said receptacle; and,
    a cap sized to removable fit over said open end.

28. A remover for removing an ectoparasite from a host organism, comprising:
    a plunger having a gas spraying orifice;
    an anesthetizing gas producing means coupled to said plunger having anesthetizing gas;
    a receptacle having an open end and a closed end having a hole closed by said plunger inserted through said hole into said receptacle for injecting said anesthetizing gas through said gas spraying orifice into said receptacle.

29. The remover according to claim 28 further including a snap mechanism for holding said plunger in said hole.

30. The remover according to claim 28 wherein said receptacle further includes a closure means for closing said hole after said plunger has been removed and for closing the open end to prevent escape of the ectoparasite from said receptacle.

31. The remover according to claim 30 wherein said receptacle further includes an inside surface and said closure means includes a flap coupled to said inside surface of said closed end retractably covering said hole.

32. The remover according to claim 31 wherein said closure means further includes a cap for covering said open end.

33. The remover according to claim 31 wherein said closure means includes a first pressure sensitive tape for covering said hole and a second pressure sensitive tape for covering said open end.

34. A remover for removing an ectoparasite from a host organism, comprising:

a receptacle having:
   an open end; and,
   a closed end having a plunger with a gas spraying orifice integrally formed with said closed end; and, an anesthetizing gas producing means coupled to said plunger having anesthetizing gas for injection through said gas spraying orifice into said receptacle.

35. A remover for removing an ectoparasite from a host organism, comprising:

a receptacle having:
   an open end; and,
   a closed end with a sleeve;

a plunger coupled to said receptacle at said closed end and having a gas spraying orifice;

a pressurized gas container having anesthetizing gas; and said sleeve snugly receiving said pressurized gas container for injection of said anesthetizing gas through said gas spraying orifice into said receptacle.

* * * * *